US00PP29267P2

(12) United States Plant Patent
Deng

(10) Patent No.: US PP29,267 P2
(45) Date of Patent: May 1, 2018

(54) ***LANTANA CAMARA* PLANT NAMED 'UF-1011-2'**

(50) Latin Name: ***Lantana camara* L. (*Lantana strigocamara* R.W. Sanders)**
Varietal Denomination: UF-1011-2

(71) Applicant: Florida Foundation Seed Producers, Inc., Marianna, FL (US)

(72) Inventor: Zhanao Deng, Riverview, FL (US)

(73) Assignee: Florida Foundation Seed Producers, Inc., Marianna, FL (US)

( * ) Notice: Subject to any disclaimer, the term of this patent is extended or adjusted under 35 U.S.C. 154(b) by 0 days. days.

(21) Appl. No.: 15/530,166

(22) Filed: Dec. 8, 2016

(51) Int. Cl.
*A01H 5/00* (2018.01)

(52) U.S. Cl.
USPC ..... Plt./227

(58) Field of Classification Search
USPC ..... Plt./227
See application file for complete search history.

(56) References Cited

PUBLICATIONS

Czarnecki II, David M. et al., Ploidy Levels and Pollen Stainability of *Lantana camara* Cultivars and Breeding Lines, HortScience 49(10):1271-1276, 2014.
Czarnecki II, David Mark, Genetic Sterilization and Reproductive Biology of *Lantana camara,* A Dissertation Presented to the Graduate School of the University of Florida in Partial Fulfillment of the Requirements for the Degree of Doctor of Philosophy, University of Florida, 2011, 210 Pages.
Czarnecki II, David M. et al., UF-T3 and UF-T4: Two Sterile *Lantana camara* Cultivars, HortScience vol. 47(1):132-137, Jan. 2012.

*Primary Examiner* — Susan McCormick Ewoldt
(74) *Attorney, Agent, or Firm* — Christopher & Weisberg, P.A.

(57) ABSTRACT

A new and distinct cultivar of *Lantana camara* plant named 'UF-1011-2', characterized by its moderate vigor, mounding growth habit, dense branching, round plant form and canopy, free flowering, bright yellow and magenta flowers, little fruiting, few seeds, high level of female infertility, low level of pollen stainability, high level of male infertility, and lack of hybridization with *Lantana depressa.*

2 Drawing Sheets

ACKNOWLEDGMENT OF FEDERAL RESEARCH SUPPORT

This invention was made with government support under FLA-GCR-005065 and FLA-GCR-005507 awarded by the National Institute of Food and Agriculture, USDA. The government has certain rights in the invention.

Genus and species: *Lantana camara* L. (*Lantana strigocamara* R. W. Sanders).

Cultivar denomination: 'UF-1011-2'.

CROSS-REFERENCE TO RELATED APPLICATION n/a

BACKGROUND OF THE NEW CULTIVAR

The present invention relates to a new and distinct cultivar of *lantana*, botanically known as *Lantana camara*, and hereinafter referred to by the name 'UF-1011-2'.

*Lantana camara* is a member of Verbenaceae. Plants of this species attract numerous species of butterflies, tolerate harsh environmental conditions, have low maintenance requirements, and are easy to grow. Plants of *L. camara* are highly desirable for use in containers, hanging baskets, and landscapes. Commercial production of *L. camara* is widespread in the nursery industry, especially in the southern United States. This species has escaped cultivation through fruit/seed dispersal and has hybridized (as pollen donors)

with *Lantana depressa*, a rare species native to Florida, resulting in its classification as a Category I invasive species in Florida (Florida Exotic Pest Plant Council, 2015). There has been a strong need for the development of infertile cultivars in *L. camara.*

The new *Lantana* cultivar 'UF-1011-2' is a product of a planned breeding program in Balm, Fla. The primary objective of the breeding program is to create new infertile *lantana* cultivars with desirable plant stature, dense branching habits, and attractive flower colors.

The new *Lantana* cultivar 'UF-1011-2' originated from a planned cross between a proprietary breeding line CAOP-73 and cultivar 'Landmark Flame Improved' ('Balandimfla', an abandoned U.S. Plant patent application Ser. No. 11/015,489). The stated cross was made in fall 2010 in Balm, Fla. The new *Lantana* cultivar 'UF-1011-2' was discovered and selected in Balm, Fla. in April 2012 as one flowering plant within the progeny of the stated cross.

Asexual propagation of the new *Lantana* cultivar 'UF-1011-2' by vegetative cuttings in a controlled environment in Balm, Fla. since 2012 has shown that the unique features of this new *lantana* are stable and reproduce true to type in successive generations.

Plant Breeder's Rights for this cultivar have not been applied for. The new *Lantana* cultivar 'UF-1011-2' has not been made publicly available more than one year prior to the filing of this application.

SUMMARY OF THE INVENTION

The new *Lantana* cultivar 'UF-1011-2' has not been observed under all possible environmental conditions. The phenotype of the new cultivar may vary with variations in environment and cultural practices such as temperature, light intensity, fertilization, irrigation, and application of plant growth regulators without any change in genotype.

The following traits have been repeatedly observed and are determined to be the unique characteristics of the new *Lantana* cultivar 'UF-1011-2'. These characteristics in combination distinguish 'UF-1011-2' as a new and distinct cultivar of *Lantana:*

1. moderate plant vigor;
2. mounding growth habit;
3. dense branching;
4. round plant form and canopy;
5. yellow and magenta flowers;
6. little fruiting and no or few berries, little seed production, and high level of female infertility;
7. low pollen stainability and high level of male infertility; and
8. no to little hybridization potential with *Lantana depressa.*

Plants of the new *Lantana* cultivar 'UF-1011-2' differ from plants of the female parent in the following characteristics:

1. plants of 'UF-1011-2' are triploids, while plants of CAOP-73 are tetraploids;
2. plants of 'UF-1011-2' are mounding, while plants of CAOP-73 are more upright and erratic;
3. plants of 'UF-1011-2' produce no or few fruit, no or few seeds, and are highly female-infertile, while plants of CAOP-73 are more female-fertile and produce more fruit; and
4. plants of 'UF-1011-2' have low pollen stainability or viability, while plants of CAOP-73 have much higher pollen stainability or viability.

Plants of the new *Lantana* cultivar 'UF-1011-2' differ from plants of the male parent, 'Landmark Flame Improved', in the following characteristics:

1. plants of 'UF-1011-2' are triploids, while plants of 'Landmark Flame Improved' are diploids;
2. plants of 'UF-1011-2' are compact and mounding and have a round form and canopy, while plants of 'Landmark Flame Improved' are much larger, spreading, and have an open canopy;
3. flowers of 'UF-1011-2' are yellow-colored when initially open and turn magenta when matured, while flowers of 'Landmark Flame Improved' are gold to orange;
4. plants of 'UF-1011-2' produce no or few fruit or seeds and are highly female-infertile, while plants of 'Landmark Flame Improved' are female-fertile and produce more fruit and seeds; and
5. plants of 'UF-1011-2' have low pollen stainability or viability, while plants of 'Landmark Flame Improved' have much higher pollen stainability or viability.

Plants of the new *Lantana* cultivar 'UF-1011-2' can be compared to 'Bandana® Cherry Sunrise' ('Bante Cheriasun', U.S. Plant Pat. No. 19,264). In side-by-side comparisons conducted in Balm, Fla., plants of the new *Lantana* cultivar 'UF-1011-2' differed from plants of 'Bandana® Cherry Sunrise' in the following characteristics:

1. plants of 'UF-1011-2' are taller and wider than plants of 'Bandana® Cherry Sunrise'; and
2. plants of the new cultivar 'UF-1011-2' have longer internodes than plants of 'Bandana® Cherry Sunrise'.

Plants of the new *Lantana* cultivar 'UF-1011-2' can be compared to 'Landmark™ Sunrise Rose' ('Balandrosim', U.S. Plant Pat. No. 21,764). In side-by-side comparisons conducted in Balm, Fla., plants of the new *Lantana* cultivar 'UF-1011-2' differed from plants of 'Landmark™ Sunrise Rose' in the following characteristics:

1. plants of 'UF-1011-2' have a more round form and canopy, while plants of 'Landmark™ Sunrise Rose' have a more open canopy with fewer lateral branches; and
2. plants of 'UF-1011-2' are fuller and shorter than plants of 'Landmark™ Sunrise Rose'.

DESCRIPTION OF THE FIGURES

The accompanying photographs (as shown in FIGS. 1 and 2) illustrate the overall appearance of the new *Lantana* cultivar 'UF-1011-2'. These photographs show the colors as true as can be reasonably obtained in colored reproductions of this type. Colors in the photographs may differ slightly from the color values cited in the detailed botanical description, which accurately describe the colors of the new *Lantana* cultivar.

DETAILED BOTANICAL DESCRIPTION OF THE CULTIVAR

Figure 1:
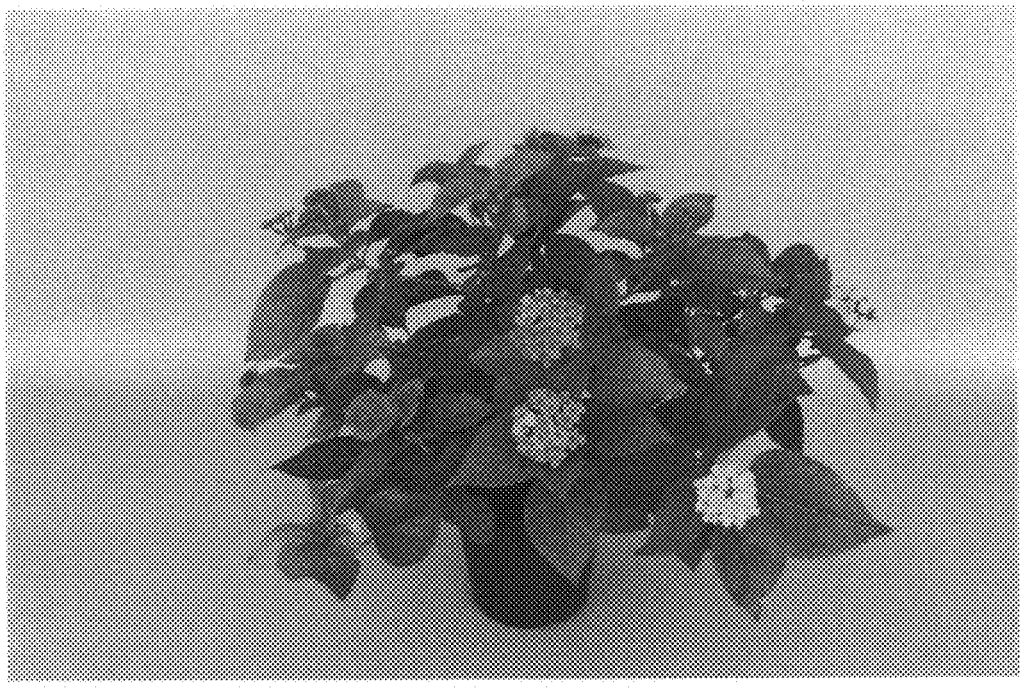
FIG. 1 shows a side perspective view of a typical flowering plant of the new cultivar to show its growth and branching habit, plant form, and flower colors. The plant was grown in a 10.2-cm container in the summer of 2016 in Balm, Fla. for 13 weeks from when terminal cuttings were made. The plant was pinched at four weeks after the cuttings were stuck and sprayed once with growth retardants at six weeks after the cuttings were stuck.
Figure 2:
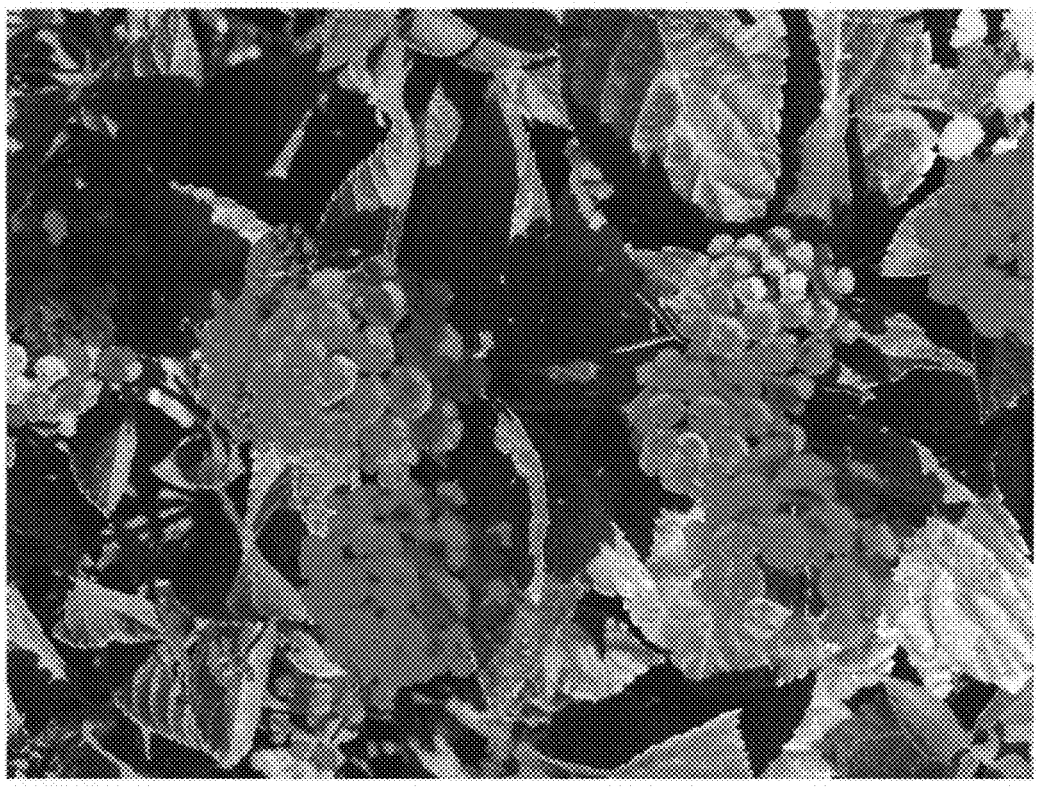
FIG. 2 shows a close-up view of typical inflorescences and flower colors of the new cultivar. Plants of the new cultivar were grown outdoors in ground beds in full sun in Balm, Fla. The plants were propagated by cuttings, container-grown in a soilless mix for 95 days, transplanted to the ground bed in the week of Jun. 12, 2015, and grown in the ground for 124 days. The photo was taken in Balm, Fla. on Oct. 14, 2015.

In the following description, color references are made to The Royal Horticultural Society (R.H.S.) Colour Chart, 1986 Edition, except where general terms of ordinary dictionary significance are used. The features of 'UF-1011-2' described herein are shown in FIGS. 1 and 2.

DESCRIPTION OF GROWING CONDITIONS

Plants used for the description were grown in the summer of 2016 in Balm, Fla. for 11 weeks from when terminal cuttings were made. Plants were planted in a 10.2-cm container and only pinched at four weeks after the cuttings were stuck into the rooting medium and sprayed once with growth retardants at six weeks after the cuttings were stuck. Plants were grown outdoors for three weeks in early September in Balm, Fla. before flower color descriptions were made. During the production of the plants in the polypropylene-covered shadehouse, temperatures ranged from about 22.2° C. to about 35.5° C.

BOTANICAL DESCRIPTION

Botanical classification:

*Family*.—Verbenaceae.

*Botanical name*.—*Lantana camara* L. (*Lantana strigocamara* R. W. Sanders).

*Common name*.—*Lantana*.

*Cultivar*.—'UF-1011-2'.

Parentage:

*Female or seed parent*.—Parent from breeding line CAOP-73.

*Male or pollen parent*.—'Landmark Flame Improved'.

Propagation:

*Type*.—Terminal cutting.

*Time to initiate roots, summer*.—Approximately ten days at 27° C.

*Time to initiate roots, winter*.—Approximately ten days at 27° C.

*Time to develop roots, summer*.—Approximately 21 days at 27° C.

*Time to develop roots, winter*.—Approximately 21 days at 27° C.

Root description: Fine, fibrous.

*Color*.—Close to white (RHS 155B) initially, then becoming closer to greyed- brown (RHS 199C) and streaks of greyed-yellow (RHS 161C) with development.

*Rooting habit*.—Freely branching.

Plant description:

*Type*.—Flowering subshrub.

*Plant form*.—Upright and slightly spreading plant habit.

*Growth habit*.—Mounded round plant form; dense branches; two lateral branches potentially forming at every node; pinching enhances lateral branch development.

*Plant height*.—Approximately 23 cm.

*Plant diameter*.—Approximately 35 cm×25 cm.

*Lateral branches*.—Length: Approximately 13.3 cm. Diameter: Approximately 2.5 mm. Internode length: Approximately 2.4 cm. Strength: Strong, but flexible. Texture: Rough, pubescent. Color, young: Close to yellow-green (RHS 144A). Color, woody: Close to greyed-brown (RHS 199B).

*Stem*.—Quantity of main branches per plant: Approximately seven to eight. Quantity of leaves per branch: Approximately 13-15. Length of stem: Approximately 17-19 cm. Diameter: Approximately 4 cm. Length of internodes: Approximately 1.5-2.5 cm. Texture: Pilose and having a few glandular hairs. Color, young: Close to yellow-green (RHS 144A). Color, woody: Close to greyed-brown (RHS 199C) with streaks of greyed-brown (RHS 199A).

Foliage description:

*Arrangement*.—Opposite; simple.

*Length*.—Approximately 6.5-8 cm.

*Width*.—Approximately 4-5 cm.

*Shape*.—Ovate. Apex: Acute. Base: Obtuse with truncate tendencies.

*Margin*.—Serrate.

*Teeth along margins per leaf*.—Approximately 29-39.

*Texture, upper and lower surfaces*.—Leathery, rough, coarse; pubescent.

*Luster*.—Upper surface: Slightly glossy. Lower surface: Dull.

*Color, developing and fully expanded foliage*.—Upper surface, developing: Close to green (RHS 137C). Upper surface, expanded: Close to green (RHS 137A). Lower surface, developing: Close to green (RHS 137C). Lower surface, expanded: Close to green (RHS 137B).

*Venation pattern*.—Pinnate, arcuate.

*Color of veins*.—Upper surface: Close to green (RHS 137A). Blends in with the leaf color. Lower surface: Close to yellow-green (RHS 144D) for the midrib; primary veins are close to yellow-green (RHS 148C).

*Petiole*.—Length: Approximately 1.3-2.3 cm. Diameter: Approximately 1.5 mm. Texture, both surfaces: Slightly pubescent. Color: Upper surface: Close to yellow-green (RHS 144A). Lower surface: Close to yellow-green (RHS 144C).

Inflorescence description:

*Flower type*.—Small salverform flowers arranged in axillary umbels. Flowers face mostly upward or outward.

*Flowering habit*.—Very freely flowering, with potentially two inflorescences per node. Typically about 21-25 flowers per umbel, flowering continuous and consistent, spring until late frost in the autumn.

*Flowering longevity on the plant*.—Approximately one week.

*Fragrance*.—Faint, pleasant.

*Inflorescence diameter*.—Approximately 4 cm.

*Inflorescence height*.—Approximately 2.3 cm.

*Number of flowers per inflorescence*.—Approximately 21-25.

*Quantity of inflorescences per plant*.—Approximately 18-23.

*Flower appearance*.—Flared trumpet, corolla fused, four-parted. Flowers are roughly rectangular in shape.

*Flower diameter*.—Approximately 1 cm×1 cm.

*Flower buds* (*before showing color*).—Length: Approximately 4 mm. Diameter: Approximately 5 mm. Shape: Roughly spherical to ovoid. Color: Close to yellow-green (RHS 144C).

*Bract*.—Length: Approximately 4 mm. Diameter: Approximately 1 mm. Color: Yellow-green (RHS 144D) with yellow-green (RHS 144A) at the apex. Texture: Outer surface: Hirsute. Inner surface: Glandular hairs on the inner surface.

*Corolla*.—Arrangement/appearance: Single whorl of four petals, fused into flared trumpet. Tube length: Approximately 1.2 cm. Throat and tube texture: Outer surface: Pubescent/slightly hirsute basally. Inner surface: Papillose. Tube color (mature): Outer surface: Close to red-purple (RHS 61A). Inner surface: Throat, close to red-purple (RHS 62D).

*Petal*.—Length from throat: Upper and lower petals. Approximately 5.5 mm. Lateral petals: Approximately 5 mm. Width: Upper and lower petals: Approximately 6.5 mm. Lateral petals: Approximately 4 mm. Shape: Spatulate to somewhat rectangular. Apex: Rounded. Margin: Entire. Degree of lobation: Slightly overlapping lobes. Petal lobe texture, upper and lower surfaces: Smooth, velvety. Color: Petal lobes, when opening (immature): Upper surface: Close to yellow-orange (RHS 14A) and changes close to orange (RHS 24A). Eye color:

None. Lower surface: Close to yellow-orange (RHS 14D) and other surfaces close to red (RHS 39B). Petal lobes, fully opened (mature): Upper surface: Close to red-purple (RHS 67A). Lower surface: Close to red-purple (RHS 68D). Throat: Close to red-purple (RHS 62D). Tube: Close to red-purple (RHS 61A).

*Calyx*.—Number of sepals: One sepal per flower. Length: Approximately 5.5 mm. Width: Approximately 1 mm. Shape: Lanceolate. Apex: Acute. Base: Truncate. Texture: Upper surface: Pubescent. Lower surface (inside): Pubescent. Color: Apex: Close to yellow-green (RHS 144A). Base: Close to yellow-green (RHS 144C).

*Peduncles*.—Length: Approximately 4.5-6.5 cm. Diameter: Approximately 1.2 mm. Angle: Approximately 45° from the stem. Strength: Flexible, but strong. Texture: Pubescent. Color: Close to yellow-green (RHS 144B).

*Pedicels*.—Not observed, flowers not stalked.

*Stamens*.—Quantity/arrangement: Four per flower, adnate to floral tube. Length of filament: Approximately 4 mm. Color of filament: Close to white (RHS 155C).

*Anther*.—Shape: Oblong. Length: Approximately 1 mm. Color close to yellow (RHS 9C).

*Pistils*.—Quantity: One per flower. Length: Approximately 3 mm. Stigma shape: Oblong. Color: Close to yellow-green (RHS 144C).

*Ovary color*.—Close to yellow-green (RHS 144B).

*Pollen*.—Amount: Rarely observed.

*Fruit*.—Amount: Rarely observed.

COMPARISON WITH KNOWN CULTIVARS

Assessment of Female Fertility

Table 1 shows fruit production, seed viability, seed germination, and female fertility of the new *Lantana* cultivar 'UF-1011-2' and two check cultivars in two replicated field trials in Florida. The check cultivars are 'UF-T3' (U.S. Plant Pat. No. 24,057) and 'Pink Caprice' (commercial cultivar, not patented).

Plants in the two trials were grown in ground beds in full sun in Balm (southwest Florida, USDA hardiness zone 9A and AHS heat zone 10) and in Ft. Pierce (southeast Florida, USDA hardiness zone 9B and AHS heat zone 9-10). The experimental design used in Balm was a randomized complete block with three blocks and two plants per plot. The experimental design used in Ft. Pierce was a randomized complete block, but with four blocks and a single plant per plot. 'Pink Caprice' is very prolific in fruit (and seed) production (Czarnecki, 2011; Czarnecki et al., 2012), while 'UF-T3' is highly infertile (Czarnecki et al., 2012).

Fruit production data were regularly collected from the field-grown plants in Balm and Ft. Pierce. The four harvests in Balm were made on August 17, September 14, October 16, and Nov. 18, 2015, respectively. The four harvests in Ft. Pierce were done on August 12, September 10, October 14, and Nov. 11, 2015, respectively. In each round of fruit harvesting, 20 peduncles were randomly sampled from each plant in the replicated field trials. Drupes on all harvested peduncles were counted, regardless of maturity. An analysis of variance and separation of mean fruit production values were was conducted using the statistics software JMP Pro 10.0.2 to compare the fruit production of the new *Lantana* cultivar 'UF-1011-2' with that of 'UF-T3' and 'Pink Caprice'. Mean values with the same letter within columns in Table 1 are not significantly different by the Fisher's Least Significant Difference (LSD) procedure at $P<0.05$.

As shown in Table 1, 'Pink Caprice' produced the largest number of drupes among all the entries in the two replicated trials. Each peduncle bore an average of 7.941 drupes in Ft. Pierce and 10.313 drupes in Balm, with an overall average of 9.127 across the two sites and four harvests. The number of drupes sterile cultivar 'UF-T3' produced per peduncle ranged from 0 to 0.100 and averaged to 0.043 across two experimental sites and over 4 months. The number of drupes per peduncle for the new *Lantana* cultivar 'UF-1011-2' ranged from 0 to 0.125 and averaged to 0.033 across the two sites and over the 4 months. This level of fruit production in the new *Lantana* cultivar 'UF-1011-2' represents greater than 99% reduction from the fruit production of 'Pink Caprice'.

Seeds were extracted from mature drupes collected from the above described experiments. Seeds were cleaned, air-dried, and germinated. Due to having few seeds for the new *Lantana* cultivar 'UF-1011-2' and 'UF-T3', seeds from four harvests at each site were combined before germination. Seeds of 'Pink Caprice' were also sent to a commercial seed testing laboratory (Midwest Seed Services, Brookings, S. Dak.) for seed viability tests. The new *Lantana* cultivar 'UF-1011-2' and 'UF-T3' produced few or no seeds at either site and were not tested for viability.

As shown in Table 1, seeds of 'Pink Caprice' showed an average of 65.0% viability, germinated readily, with an average germination percentage of 45.0% in 60 days. For 'UF-T3', a total of seven and two seeds were collected from Balm and Ft. Pierce trials, respectively. One of the nine seeds germinated, resulting in an 11.1% germination. For the new *Lantana* cultivar 'UF-1011-2', there were only four seeds collected from plants at the Balm site and no seeds collected at the Ft. Pierce site. None of the four seeds germinated.

Fruit (seed) production per peduncle and seed germination are factored into a female fertility index (FFI) by multiplying fruit production per peduncle and seed germination. The FFI for 'Pink Caprice' and 'UF-T3' was 4.107, and 0.005, respectively. The FFI for the new *Lantana* cultivar 'UF-1011-2' was zero.

TABLE 1

| Lantana | Peduncles examined (no.) | | Fruit per peduncle (no.) | | |
|---|---|---|---|---|---|
| cultivar | Balm | Ft. Pierce | Balm | Ft. Pierce | Average |
| 'UF-1011-2' | 480 | 270 | 0.048 b | 0.013 b | 0.033 |
| 'UF-T3' | 480 | 320 | 0.046 b | 0.041 b | 0.044 |
| 'Pink Caprice' | 480 | 320 | 10.313 a | 7.941 a | 9.127 |

| Lantana cultivar | Seed viability (%) | Seeds planted (no.) | Seed germination (%) | Female fertility (FFI) |
|---|---|---|---|---|
| 'UF-1011-2' | — | 4 | 0 | 0 |
| 'UF-T3' | — | 9 | 11.1 | 0.005 |
| 'Pink Caprice' | 65.0 | 100 | 45.0 | 4.107 |

Assessment of Pollen Stainability

Table 2 shows pollen stainability of the new *Lantana* cultivar 'UF-1011-2' and two check cultivars ('UF-T3' and 'Pink Caprice') when their plants were grown in Balm and Ft. Pierce, Fla. in full sun in 2015. Two pollen staining experiments were conducted. In Experiment 1, newly opened flowers were collected from plants grown in Balm, Fla. in late July 2015, and anthers were extracted from the flowers and collected into a 1.5-mL Eppendorf tube. The collected anthers were stained with $10^{-6}$ M fluorescein diacetate (FDA) (Sigma-Aldrich, St. Louis, Mo.) in 0.22 M sucrose at room temperature in the dark for 1 hour (Czarnecki et al., 2014). Stained anthers were transferred onto a microscope slide and covered with a coverslip. Pollen grains in the anthers were released by gently tapping and pressing the coverslip and then examined under a fluorescent microscope. Plump, round pollen grains fluorescing bright yellowish green light were considered stainable, while misshaped, non-fluorescing, or unevenly, lightly fluorescing pollen grains were counted as non-stainable. In Experiment 2, flowers were collected from *lantana* plants grown in Ft. Pierce, Fla. in mid-August 2015. Anther staining and pollen examination were performed as described in Experiment 1.

Pollen stainability data (in percentage) were arcsine-transformed before analysis of variance was performed. Means with the same letter within the column of Table 2 are not significantly different by the LSD procedure at P<0.05. The analysis of variance and mean separation were conducted using JMP Pro 12.0.1.

As shown in Table 2, the average pollen stainability of the new *Lantana* cultivar 'UF-1011-2' was 9.7%, close to the average pollen stainability of cultivar 'UF-T3'. The average pollen stainability of 'Pink Caprice' was 73.1%, similar to previous results (Czarnecki et al., 2014). The pollen stainability (or male fertility) of the new *Lantana* cultivar 'UF-1011-2' was reduced substantially (86.7%) from that of 'Pink Caprice'.

TABLE 2

| | Pollen grains examined (no.) | | Pollen stainability (%) | | |
|---|---|---|---|---|---|
| Cultivar | Experiment 1 | Experiment 2 | Experiment 1 | Experiment 2 | Average |
| 'UF-1011-2' | 1684 | 1563 | 10.0 b | 9.4 b | 9.7 |
| 'UF-T3' | 2760 | 1752 | 5.3 c | 4.9c | 5.1 |
| 'Pink Caprice' | 1094 | 1271 | 70.8 a | 75.3 a | 73.1 |

Assessment of Hybridization Potential with *Lantana Depressa*

Table 3 shows the hybridization potential of the new *Lantana* cultivar 'UF-1011-2' with *L. depressa* as compared to 'UF-T3' and 'Pink Caprice'.

Hand pollination experiments were performed in a greenhouse in Balm, Fla. in June and July 2015 to assess the hybridization potential of the new *Lantana* cultivar 'UF-1011-2', as a male or female parent, with *L. depressa*. 'UF-T3' and 'Pink Caprice' were included in the hand pollination experiments as an infertile and a fertile check, respectively. Stock plants of all *Lantana* cultivars and *L. depressa* were grown in 1-gallon plastic containers and arranged into three blocks. The experimental unit was two containerized plants. Temperatures inside the greenhouse ranged from 21° C. to 33° C. No supplemental lighting was provided. Plants were drip-irrigated twice a day. Fresh anthers were collected from mature unopened flowers of male parents and applied immediately to emasculated flowers of female parents. At maturity, fruit produced by the pollinated flowers were collected and counted, and seeds were extracted and germinated to determine seed germination percentages.

Fruit set data (in percentage) were arcsine-transformed before analysis of variance was performed in JMP Pro 12.0.1. Means with the same letter within the column are not significantly different by the LSD procedure at P<0.05.

As a male parent, 'Pink Caprice' caused an average of 8.6% fruit set on *L. depressa*. When pollinated with *L. depressa*, 'Pink Caprice' flowers showed 19.7% fruit set. Seeds from crosses between 'Pink Caprice' and *L. depressa* or vice versa showed 11.1% or 19.7% seedling emergence. 'UF-T3' caused 0.3% fruit set on *L. depressa* flowers and showed 0.8% fruit set after being pollinated with *L. depressa*. None of the seeds emerged as seedlings.

A total of 362 *L. depressa* flowers were pollinated with the new *Lantana* cultivar 'UF-1011-2', and one flower set one fruit, resulting in average fruit set of 0.2%. The fruit contained one seed, and it failed to germinate in the greenhouse. When the new cultivar was used as the female parent, it did not set fruit after having been pollinated with *L. depressa*. Therefore, the new cultivar did not hybridize or did not produce viable progeny with *L. depressa* when they were used as a male or a female parent in hand pollinations. These data also confirm the high level of male and female infertility in the new cultivar.

TABLE 3

| Cultivar | Flowers pollinated (no.) | Fruit set (%) | Seedling emergence (%) |
|---|---|---|---|
| | *L. depressa* as the female parent | | |
| 'UF-1011-2' | 363 | 0.2 b | 0 |
| 'UF-T3' | 368 | 0.3 b | 0 |
| 'Pink Caprice' | 388 | 8.6 a | 11.1 |
| | *L depressa* as the male parent | | |
| 'UF-1011-2' | 513 | 0 b | — |
| 'UF-T3' | 467 | 0.8 b | 0 |
| 'Pink Caprice' | 452 | 19.7 a | 15.8 |

We claim:

1. A new and distinct *Lantana* plant named 'UF-1011-2' as illustrated and described herein.

* * * * *